(12) United States Patent
Nadarajah et al.

(10) Patent No.: US 11,651,294 B2
(45) Date of Patent: May 16, 2023

(54) SYSTEM AND METHOD FOR DETECTING DRUG ADVERSE EFFECTS IN SOCIAL MEDIA AND MOBILE APPLICATIONS DATA

(71) Applicant: IQVIA INC., Parsippany, NJ (US)

(72) Inventors: Sivakumar Nadarajah, Bridgewater, NJ (US); Sanmugam Aravinthan, Lake Hiawatha, NJ (US); Kannan Ramamoorthy, Edison, NJ (US)

(73) Assignee: IQVIA INC., Durham, NC (US)

( * ) Notice: Subject to any disclaimer, the term of this patent is extended or adjusted under 35 U.S.C. 154(b) by 545 days.

(21) Appl. No.: 13/974,756

(22) Filed: Aug. 23, 2013

(65) Prior Publication Data
US 2014/0058744 A1    Feb. 27, 2014

Related U.S. Application Data

(60) Provisional application No. 61/692,697, filed on Aug. 23, 2012.

(51) Int. Cl.
*G06Q 10/00* (2012.01)
*G16H 20/10* (2018.01)
*G16H 70/40* (2018.01)

(52) U.S. Cl.
CPC ............. *G06Q 10/00* (2013.01); *G16H 20/10* (2018.01); *G16H 70/40* (2018.01)

(58) Field of Classification Search
CPC ............................... G06Q 50/22; G06Q 50/24
See application file for complete search history.

(56) References Cited

U.S. PATENT DOCUMENTS 6,813,615 B1   11/2004  Colasanti et al.
7,379,885 B1 *  5/2008  Zakim ............................... 705/2
(Continued)

FOREIGN PATENT DOCUMENTS

WO   WO2008042993 A3   11/2008
WO   WO-2013006783 A1 *  1/2013   ........... G06F 19/363

OTHER PUBLICATIONS

Kamel Boulos, Maged N., and Steve Wheeler. "The emerging Web 2.0 social software: an enabling suite of sociable technologies in health and health care education 1." Health Information & Libraries Journal 24.1 (2007): 2-23. (Year: 2007).*
International Search Report and Written Opinion dated Dec. 30, 2013 from corresponding International Application No. PCT/US2013/056460, 18 pages.
(Continued)

*Primary Examiner* — Lena Najarian
(74) *Attorney, Agent, or Firm* — John Maldjian; Stevens & Lee PC

(57) ABSTRACT

Some implementations provide a computer-implemented method for identifying, from on-line postings, reports of potential adverse effects resulting from consuming a healthcare product, the method including: receiving a log of on-line postings regarding consuming the healthcare product; receiving a database comprising a healthcare taxonomy and a set of linguistic rules; analyzing, based on the healthcare taxonomy, the log of on-line postings to identify a report of at least one adverse effect resulting from consuming the healthcare product; generating a score for the identified report according to the healthcare taxonomy and the set of linguistic rules; comparing the generated score with a threshold; and in response to determining that the generated score is above the threshold, flagging the identified report as a report of a potential adverse effect.

32 Claims, 13 Drawing Sheets

(56) References Cited

U.S. PATENT DOCUMENTS

| | | | |
|---|---|---|---|
| RE40,979 E | 11/2009 | Vinson | |
| 7,877,086 B2 | 1/2011 | Jagadeesan et al. | |
| 7,953,746 B1 | 5/2011 | Garg et al. | |
| 8,156,240 B2 | 4/2012 | Silberstein et al. | |
| 2006/0004702 A1* | 1/2006 | St. John | G06F 16/954 |
| 2008/0172595 A1 | 7/2008 | Schmidt | |
| 2008/0243548 A1* | 10/2008 | Cafer | G06F 3/04817 |
| | | | 705/3 |
| 2009/0193085 A1 | 7/2009 | Estes | |
| 2011/0077950 A1* | 3/2011 | Hughston | G06Q 40/08 |
| | | | 705/1.1 |
| 2012/0089616 A1 | 4/2012 | Sa'adon | |
| 2012/0165989 A1 | 6/2012 | Han et al. | |
| 2012/0296894 A1* | 11/2012 | Spector | G06F 19/322 |
| | | | 707/722 |
| 2013/0013332 A1* | 1/2013 | Frieder | G06F 19/363 |
| | | | 705/2 |
| 2013/0151330 A1* | 6/2013 | Evancich | G06Q 30/0201 |
| | | | 705/14.41 |
| 2013/0339457 A1* | 12/2013 | Freire | G06Q 50/01 |
| | | | 709/206 |

OTHER PUBLICATIONS

Search Report issued in corresponding European Patent Application No. 13831165.9, dated Jun. 2, 2015, 3 pages.
Search Report issued in corresponding European Patent Application No. 1381165.9, dated Sep. 31, 2017.

* cited by examiner

SYSTEM AND METHOD FOR DETECTING DRUG ADVERSE EFFECTS IN SOCIAL MEDIA AND MOBILE APPLICATIONS DATA

CROSS-REFERENCE TO RELATED APPLICATION

This application claims the benefit of U.S. Application No. 61/692,697, filed Aug. 23, 2012. The contents of which is incorporated by reference.

BACKGROUND

The advent of the Internet, social media and mobile applications ("apps") has provided a new venue for consumers to exchange information on a healthcare product. Consumers may comment on a wide variety of subjects using social media, mobile apps and other venues where user generated content (UGC) is allowed

OVERVIEW

In one aspect, some implementations provide a computer-implemented method for identifying, from on-line postings, reports of potential adverse effects resulting from consuming a healthcare product, the method including: receiving a log of on-line posting or comments written on a mobile app regarding consuming the healthcare product; receiving a database comprising a healthcare taxonomy and a set of linguistic rules; analyzing, based on the healthcare taxonomy, the log of on-line postings to identify a report of at least one adverse effect resulting from consuming the healthcare product; generating a score for the identified report according to the healthcare taxonomy and the set of linguistic rules; comparing the generated score with a threshold; and in response to determining that the generated score is above the threshold, flagging the identified report as a report of a potential adverse effect.

Implementations may include one or more of the following features. The step of receiving the log of on-line postings may include receiving the log from a social networking web-site, an on-line discussion forum, an on-line app-store, data stored on a mobile device or a blogging web-site. The step of receiving the log of on-line postings may include receiving the log through a meta search engine, a feed aggregation engine, or a content import engine. The step of receiving the log through a feed aggregation engine may specifically include receiving the log through a Rich Site Summary (RSS) feed reader, an atom syndication feed reader, Application Program Interface (API) calls, or a JavaScript Object Notation (JSON) feed reader.

The step of analyzing the log of on-line postings may include tracking the on-line postings for a period of at least two months. The step of analyzing the log of on-line postings may include text mining the log of on-line postings based on natural language processing using the set of linguistic rules. The step of text mining the log of on-line postings may include searching for on-line postings with an identifiable patient, an identifiable reporter, a description of the adverse effect, and a description of the healthcare product being consumed. The step of text mining the log of on-line postings may include identifying typographic errors in the on-line postings based on a dictionary spelling checker or a discussion context of the on-line postings. The step of text mining the log of on-line postings may further include correcting the identified typographic errors according to the dictionary spelling checker, the discussion context of the on-line postings, a special meaning in the context of the adverse effect, or a special meaning in the context of the healthcare product.

The step of generating a score for the identified report of adverse effect may include scoring an identified report based on contributions from: (i) a proximity of keywords in the on-line postings, (ii) a discussion context of the on-line postings, (iii) a specificity of the reference by the on-line postings to the adverse effect, or (iv) a relevancy degree of the on-line postings to the healthcare product. Generating a score for the identified report of adverse effect may further include: combining the contributions by weighing previous manual inspections from a human expert for a comparable adverse effect or a comparable healthcare product.

The step of flagging the identified report may include altering a human expert of the report of potential adverse effect. The step of alerting the human expert comprises sending an email alert, a short message service (SMS) message, or a voicemail. The step of alerting the human expert may also include detecting duplicate reports of the potential adverse effect; and consolidating the detected duplicate reports. The step of receiving the database may include receiving a database including a revised healthcare taxonomy or a revised set of linguistic rules based on results of manual inspections of the flagged report by the human expert.

In another aspect, some implementations may include a computer system comprising at least one processor configured to perform the operations of: receiving a log of on-line postings regarding consuming the healthcare product; receiving a database comprising a healthcare taxonomy and a set of linguistic rules; analyzing, based on the healthcare taxonomy, the log of on-line postings to identify a report of at least one adverse effect resulting from consuming the healthcare product; generating a score for the identified report according to the healthcare taxonomy and the set of linguistic rules; comparing the generated score with a threshold; and in response to determining that the generated score is above the threshold, flagging the identified report as a report of potential adverse effect.

Implementations may include one or more of the following features. The operation of analyzing the log of on-line postings may include tracking the on-line postings for a period of at least two months. The operation of analyzing the log of on-line postings may include text mining the log of on-line postings based on natural language processing using the set of linguistic rules. The operation of text mining the log of on-line postings may include searching for on-line postings with an identifiable patient, an identifiable reporter, a description of the adverse effect, and a description of the healthcare product being consumed. The operation of text mining the log of on-line postings may include identifying typographic errors in the on-line postings based on a dictionary spelling checker or a discussion context of the on-line postings. The operation of text mining the log of on-line postings may further include correcting the identified typographic errors according to the dictionary spelling checker, the discussion context of the on-line postings, a special meaning in the context of the adverse effect, or a special meaning in the context of the healthcare product.

The operation of generating a score for the identified report of adverse effect may include scoring an identified report based on contributions from: (i) a proximity of keywords in the on-line postings, (ii) a discussion context of the on-line postings, (iii) a specificity of the reference by the on-line postings to the adverse effect, or (iv) a relevancy degree of the on-line postings to the healthcare product.

Generating a score for the identified report of adverse effect may further include: combining the contributions by weighing previous manual inspections from a human expert for a comparable adverse effect or a comparable healthcare product.

The operation of flagging the identified report may include altering a human expert of the report of potential adverse effect. The operation of alerting the human expert comprises sending an email alert, a short message service (SMS) message, or a voicemail. Alerting the human expert may also include detecting duplicate reports of the potential adverse effect; and consolidating the detected duplicate reports. The operation of receiving the database may include receiving a database including a revised healthcare taxonomy or a revised set of linguistic rules based on results of manual inspections of the flagged report by the human expert.

In yet another aspect, some implementations include a computer-readable medium, comprising software instructions, which software instructions when executed by one or more processors of a computer, causes the computer to perform the operations of: receiving a log of on-line postings regarding consuming the healthcare product; receiving a database comprising a healthcare taxonomy and a set of linguistic rules; analyzing, based on the healthcare taxonomy, the log of on-line postings to identify a report of at least one adverse effect resulting from consuming the healthcare product; generating a score for the identified report according to the healthcare taxonomy and the set of linguistic rules; comparing the generated score with a threshold; and in response to determining that the generated score is above the threshold, flagging the identified report as a report of potential adverse effect.

Implementations of the above techniques include a method, computer program product and a system. The computer program product is suitably embodied in a non-transitory machine-readable medium and includes instructions executable by one or more processors. The instructions are configured to cause the one or more processors to perform the above described actions.

The system includes one or more processors and instructions embedded in a non-transitory machine-readable medium that are executable by the one or more processors. The instructions, when executed, are configured to cause the one or more processors to perform the above described actions. The default position is not to use any external databases, but the system could be configured to perform a database check if needed.

The details of one or more aspects of the subject matter described in this specification are set forth in the accompanying drawings and the description below. Other features, aspects, and advantages of the subject matter will become apparent from the description, the drawings, and the claims.

DESCRIPTION OF DRAWINGS

FIG. 4B shows another example user interface for displaying summary status of identified leads to adverse effects.

FIG. 4H show yet still another example user interface for presenting an identified lead to adverse effects once the lead has been confirmed.

DETAILED DESCRIPTION

This disclosure generally describes a system and method for combing through vast amounts of postings at on-line communities such as social networking web-sites to identify potential reports of adverse effects from consuming a healthcare product. A feed reader may tracks one or more on-line communities. The tracking can be done in real-time through a feed reader as the comments are posted. The tracking can also be done in a batch after the on-line postings have reached a certain size or on an hourly or daily basis. The postings may be scanned based on a database that includes a healthcare taxonomy and a set of linguistic rules. The healthcare taxonomy may incorporate standard libraries such as the Medical Subject Headings (MeSH) as provided by the National Library of Medicine. The taxonomy may also include custom components specific to a healthcare product or a medical condition. These custom components may be tuned to the healthcare product or medical condition based on feedback given by a human expert on similar or comparable postings in the past. In an adaptive manner, the set of linguistic rules may also be revised based on feedback from the human expert or past experience. As the postings are analyzed for their contents, these postings may be scored in an effort to quantify the likelihood and veracity of reporting an adverse effect resulting from consuming the healthcare product. The scores of the postings may be compared to a threshold value. When the threshold value has been surpassed, the corresponding postings or the mentioned adverse effect or healthcare product may be flagged as potential leads of adverse effects. In some implementations, such potential leads of adverse effects may be sent to a human expert for manual inspection and analysis. Depending on the circumstances, the potential leads of adverse effects may be reported to regulatory agencies such as the Federal Drug Administration (FDA), EMA (European Medicines Agency) of the European Union, MHRA (Medicines and Healthcare Products Regulatory Agency (MHRA) of United Kingdom.

Figure 1:
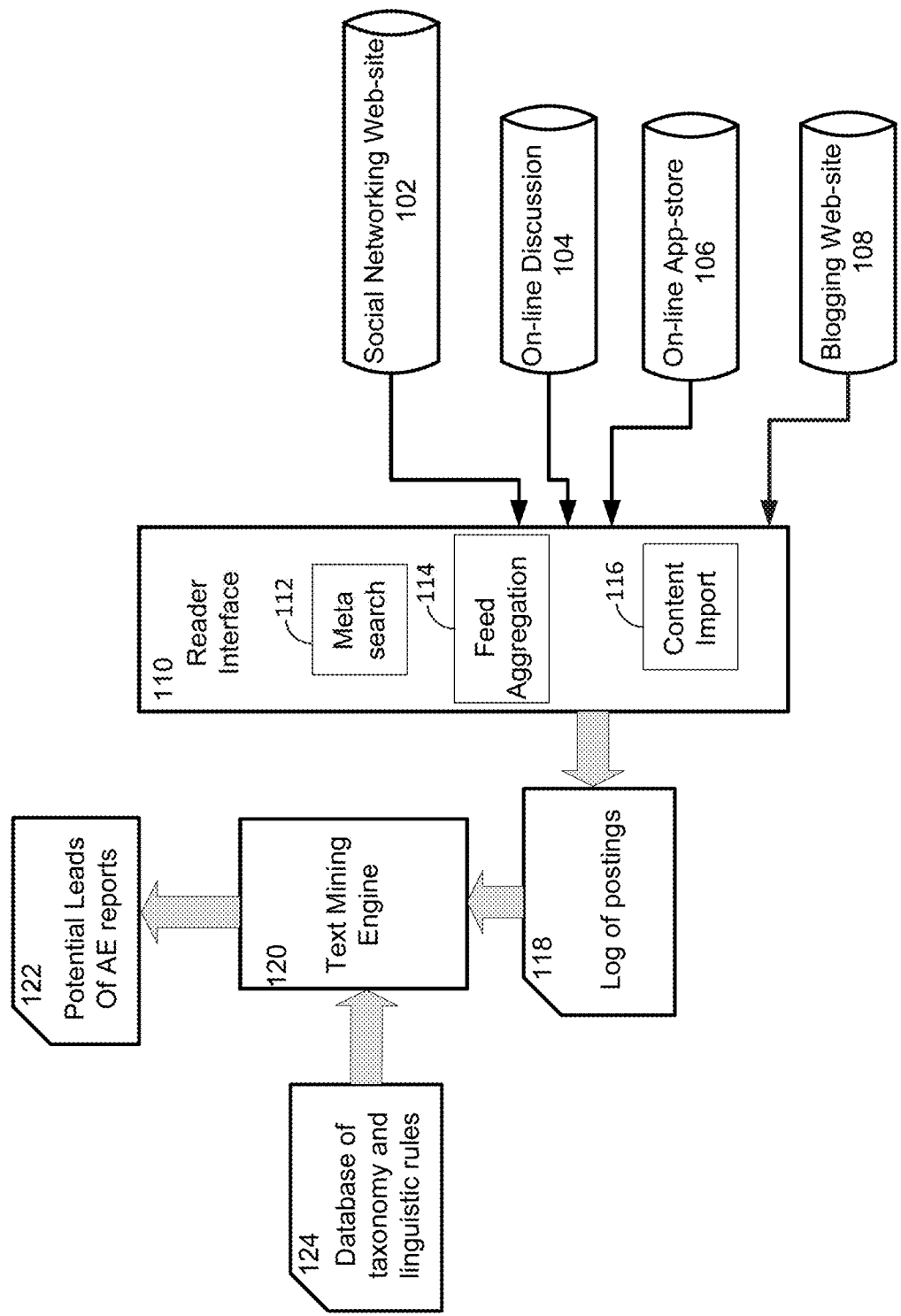
FIG. 1 is a diagram illustrating processing of feeds from voluminous on-line postings to identify potential reports of adverse effects (AE) according to some implementations.

FIG. 1 is a diagram illustrating processing feed from voluminous on-line postings to identify potential reports of adverse effects (AE) according to some implementations. As access to Internet social media become more ubiquitous, Internet users may discuss healthcare products at a myriad of on-line communities. A healthcare product may generally include any substantive or service related to health care.

Example healthcare products may include but are not limited to prescription pharmaceuticals, over-the-counter (OTC) drugs or devices, alternative medicine products or treatments, dietary supplements, cosmetics, etc. When people are considering a healthcare product, they may pose questions to elicit responses from consumers who may have used the healthcare product or similar consumer healthcare products before. The question posed can lead to an on-line discussion thread in which participants may provide information on the healthcare product at issue. The participants may also discuss related or comparable healthcare product in this on-line discussion thread. For example, the participants may discuss when they started using the healthcare product, what circumstances led them to using the healthcare product, their research of the healthcare product, their own experiences in consuming the healthcare product including any subjective or objective changes since using the healthcare product. Subjective changes may refer to any bodily changes according to the human sensory organs. Objective changes may include any physiologic changes as measured by an instrument, such as body temperature, blood glucose level, etc. In one sense, these discussions may be a gold mine of information on a particular healthcare product. For example, regulators may be interested in learning about problematic situations at the earliest possible opportunity. Similarly, researchers may use this information to revise treatment regimens identify problematic criteria. Such information also may be highly valuable to manufacturers for identifying potential adverse effects. However, manual monitoring or moderating the voluminous postings, while possible in theory, can become overwhelmingly laborious in the context of the sheer volume of Internet content being produced every day and thus impractical. Some implementations provide automatic means for flagging potential leads to adverse effects associated with consuming a particular healthcare product.

As illustrated in FIG. 1, users may post comments on a social networking web-site 102. Such postings may be related to a healthcare product. For example, a Facebook user may post daily observations when consuming a healthcare product. Such observations may include any subjective or objective changes as discussed above. The postings can include information pertaining to potential adverse effects of a healthcare product. If harvested and complied, such information may be highly valuable to a healthcare product manufacturer. Facebook is just one example of a social networking web-site. Other social networking web-sites may include Twitter, MySpace, Google+, etc.

Moreover, users may discuss a healthcare product at an on-line discussion forum 104. The on-line discussion forum may be an on-line portal sponsored by the manufacturer of the healthcare product. User registration may be required in order to for a user to access the on-line portal. As such, a posting may be linked to a registered user. At the discussion forum, a registered user may be able post questions when the registered user is considering a particular healthcare product. Responses may come from fellow consumers, who may have used the particular healthcare product. Fellow consumers may attest to using the healthcare product based on their own experiences. Fellow consumers may also reveal caveats of using the healthcare product, which may not be officially published. Fellow consumers could also advise against using the healthcare product if they had encountered negative results while using the healthcare product. Fellow consumers may also advise against taking the product under certain circumstances such as certain times of day, in combination with certain foods, and/or in association with other medicines. Sometimes, fellow consumers could refer to what they heard from other consumers or earlier postings by someone else. As discussed above, the contents of such discussions may contain valuable information on any adverse effects. However, combing through seas of such information to identify meaningful, coherent, and credible mentioning of adverse effects may present a challenge to search engine development.

A healthcare product manufacturer may obtain access to contents of the on-line discussions as an anonymous user with read access. A healthcare product manufacturer may also obtain access to contents of the on-line discussions as a sponsor of the on-line discussion forum. As a sponsor, the healthcare product manufacturer may also identify a registered user through the on-line registration database. Additionally, a healthcare product manufacturer may moderate the on-line discussion forum to facilitate discussions and even elicit more specific responses. For example, a manufacturer may host their own discussion boards or configure an automated agent (an Internet bot) to interface with other forums or boards. Compiling such information to harvest descriptive mentioning of adverse effects may provide a new venue to extract useful data of adverse effect from social media, in the on-line form, as such information is posted.

Further, on-line discussions may be conducted by users of a mobile application. Example mobile applications for on-line discussions may include WeChat, Line, or Google Hangout, etc. The mobile application may be developed for any operating system including, for example, Windows, Android, iOS, etc. The mobile application may be developed using any existing or yet to be developed languages. Example languages include Java, C, C++, Python, etc. The mobile application may include a mobile application on an iPhone, an Android phone, a blackberry, an iPad, etc. The mobile application may enable a user to chip in the user's opinion or experience of using a healthcare product during an on-line discussion. The contents of the discussion may be accessible at a server maintained at an on-line app store 106. A healthcare product manufacturer may be the sponsor of a mobile application and thus may have access to the server at the on-line app-store. As discussed above, the contents of these discussions may contain valuable information about potential adverse effects associated with consuming a healthcare product.

Additionally, on-line users may document their experience at a blogging site 108. In general, blogs tend to be more thorough and detailed than shorter forms of on-line postings. Blogs may also provide a chronicle of daily or hourly experiences as a user continues a usage course. These blogs may be traced to an individual user through the registered account. The contents of these blogs may be publicly viewable, i.e., the contents may be viewable to a larger audience either from within a social circle of the user or through a search engine. These blogs may contain opinions or experiences of the author, which may be based on the author's personal observation or the author's second-hand experience acquired from users other than the author.

When posting comments on-line, the application used by the consumer may publish the contents in a manner consistent with a semantic web standard. To facilitate information processing (such as, for example, search and comparison) by computing machines, the World Wide Web Consortium (W3C) has been developing a semantic web standard for on-line publications. Generally, such standard favors description of web page contents in the metadata that is readable by web crawlers and agents. Metadata generally refers to descriptive data embedded in the source code associated with a web publication but may not be viewable to a human reader through a browser, unless the user chooses to view the source code. Newly developed web publication languages may implement the strategy of incorporating at least portions of publication contents in the metadata. Example language formats may include Resource Description Framework (RDF) language, Web Ontology Language (OWL), and Extensible Markup Language (XML), all of which may serve as an improvement over Hyper Text Markup Language (HTML).

Reader interface 110 may consolidate information read from social networking web-site 102, on-line discussion 104, on-line App-store 106, and blogging web-site 108. Reader interface may include meta-search engine 112. Notably, most of the information may be published in compliance with the semantic web standard as discussed above. Specifically, metasearch engine 112 may send user requests to several other search engines and/or databases and aggregates the results into a single list or displays the aggregated results according to the respective sources. The Web may be too large for any one search engine to index single-handedly. More comprehensive search results can be obtained by combining the results from several search engines. Users may choose to get second opinions in conducting on-line searches. In particular, metasearch engines may enable users to enter search criteria once and access several search engines simultaneously. Metasearch engines also may save the user from having to use multiple search engines separately.

Reader interface 110 may also include feed aggregation 114. Feed aggregation 114 may include multiple feed readers to combine contents from a collection of web feeds. A web feed may also be referred to as a news feed. A feed reader may include a computer program implementation. The feed reader may be configured to receive an indication of which contents at a publisher site have been updated. Based on the indication provided in the web feed, the feed reader may proceed to download the updated contents from the publisher web-site, for example, social networking web-site 102, on-line discussion forum 104, on-line app-store 106, and blogging web-site 108. The updated contents may include comments newly posted by users at the publisher site. Thus, the updates can be tracked in real-time, as the comments are being posted. Generally speaking, a web feed may include a data format used for providing feed subscribers with frequently updated content at the publisher web-site being monitored for reports of adverse effects. A variety of web feed formats may be utilized, such as, for example, rich site summary (RSS), atom syndication format per request for comments (RFC) 5023 of the Internet Engineering Task Force (IETF), or JavaScript Object Notation (JSON) feeds.

Reader interface 110 may additionally include content import 116. Content import 115 may be configured to import contents being posted at the publisher web-site, for example, social networking web-site 102, on-line discussion forum 104, on-line app-store 106, and blogging web-site 108. The import may utilize application program interfaces (APIs) to efficiently interact with, for example, the publisher web-site. For example, social networking APIs may include social sharing APIs to obtain listings of messages, get message details, etc. Social networking APIs may also include sharing analytics APIs to list snapshots of posted comments, get snapshot details, etc. Social networking APIs may additionally include user APIs to list user, obtain contact information of a user who has posted a comment, etc. Moreover, mobile app APIs may include APIs to facilitate search engines to access data associated with the mobile app. The data associated with the mobile app, for example, the contents of a WeChat discussion, may be stored on a server at the on-line app store. Mobile app APIs may enable search engines to, for example, spider or crawl the mobile app and import such data from the server at the app-store. The importation may be in real-time, as the comments are being posted. The importation may be custom, targeting, for example, comments that satisfy linguistic rules and include contents specific to a healthcare product.

Reader interface 110 may generate a log of postings 118. The log of postings can be a snapshot of comments posted at the time of taking the snapshot. The log may also be stream-based, as newer postings arrive. The log represents results found from the collection of on-line resources where consumers may be discussing the adverse effects of a particular healthcare product.

Text mining engine 120 may comb through the log 118 to identify leads to mentioning of potential adverse effects 122. In particular, text mining engine 120 may triage the log 118 by referring to a database 124. Database 124 may include a healthcare taxonomy relating to the adverse effects and a set of linguistic rules. The taxonomy may include standard libraries, such as medical subject headings (MeSH) from the National Library of Medicine. The taxonomy may also be known as an ontology. For example, a query for "cancer" may return results directed to "cancer," "neoplasm," "tumor," etc., all of which may be treated as synonyms as the class of cancer under various contexts. The taxonomy may be laid out in a resource description framework (RDF) language. A SPARQL Protocol and RDF Query Language (SPARQL) may be used to retrieve or manipulate data stored in the RDF format. In addition to RDF, the definitions of classes, properties and the relationships (sometimes referred to as the schemas) between the classes or properties, may also be specified according to a web ontology language (OWL). The set of linguistic rules in the database may include rules for matching term, phrases, patterns, etc. For example, the set of linguistic rules may assign a weight for each matching term, each matching phrase, and each matching pattern. The specified term, phrase, sentence, as well as the assigned weight may be adjustable. The specified term, phrase, or sentence may be considered in determining whether a particular on-line posting is noteworthy. The manner in which the specified term, phrase, and sentences are considered in the determination may be adjustable as well, as will be discussed later herein. Based on the ontology as well as the linguistic rules, text mining engine 120 may identify leads to potential adverse effects from an ocean of information presented in the log 118.

Figure 2:
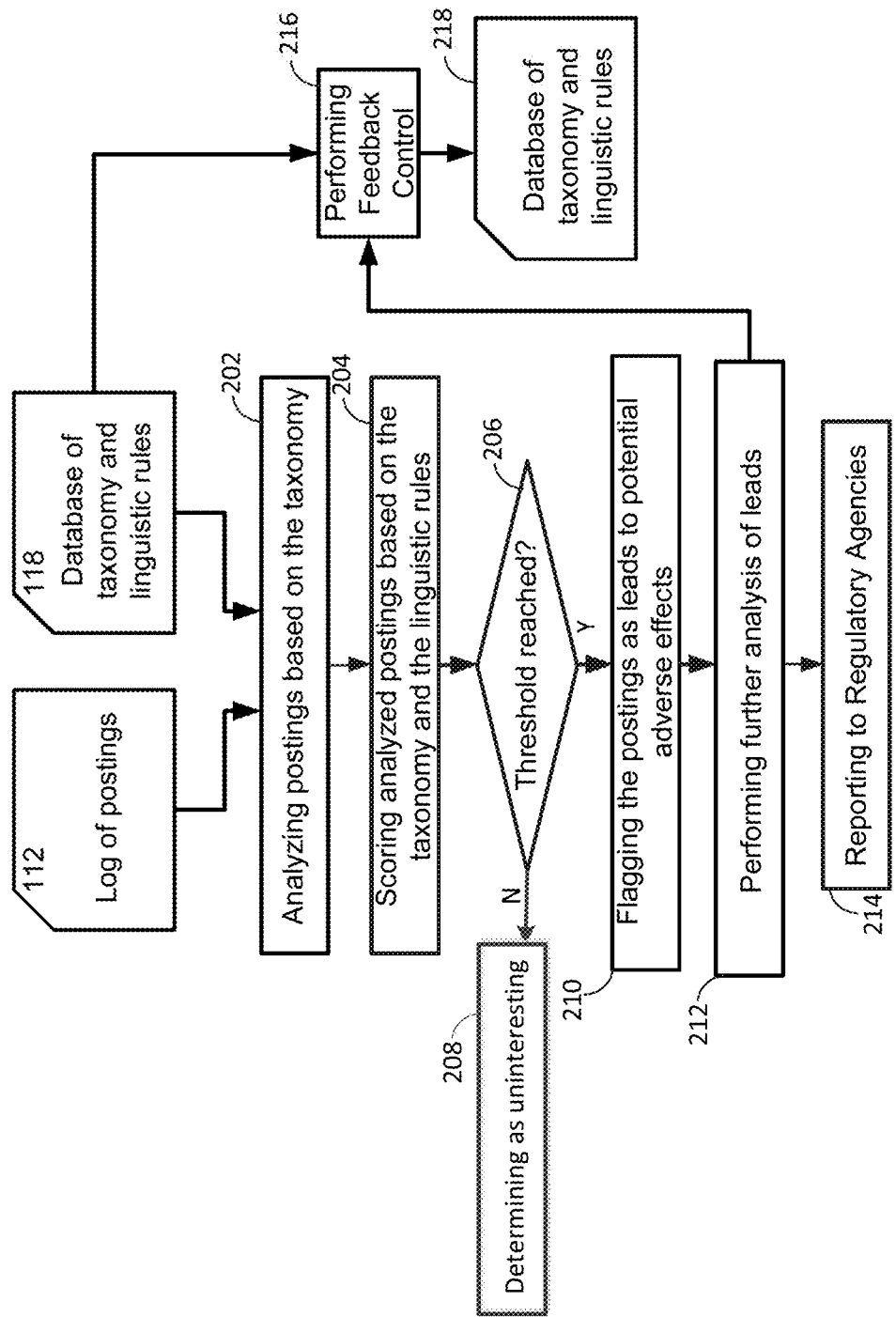
FIG. 2 is a flow chart for identifying potential AE reports in a large volume of information that may bury particular on-line postings according to some implementations.

FIG. 2 is a flow chart 200 for identifying potential AE reports in an ocean of information buried in on-line postings according to some implementations. As discussed above, log of postings 112 may include consolidated data from a myriad of on-line postings. In some implementations, contents of log 112 may be stored in a relational database. The relational database may be configured to capture the information contents of the aggregated postings. In some implementations, the relational database may store the captured information column-wise.

Database 118 may function as a dictionary in the text mining process. Database 118 may include a healthcare taxonomy. The healthcare taxonomy may include definitions for medical conditions as well as healthcare product. Medical conditions may generally refer to physical or psychological conditions being treated, or being encountered during treatment. For each listed medical condition, the taxonomy includes all synonym terms. Moreover, the taxonomy may also include a relationship of related medical conditions. For example, colon cancer may be defined as one subclass of term "cancer," terms of "nausea" and "vomiting" may be defined as companion classes as these two conditions are likely to occur concurrently; terms of "stroke" and "aneurysm" may be defined as related classes, as these two conditions may be related. In addition, the taxonomy may include trade name(s), generic name(s), brand name(s), as well as systematic names of a particular healthcare product. For example, atorvastatin, Lipitor, (3R,5R)-7-[2-(4-fluorophenyl)-3-phenyl-4-(phenylcarbamoyl)-5-propan-2-ylpyrrol-1-yl]-3,5-dihydroxyheptanoic acid may respectively be the generic name, brand name, and systematic name of one prescription drug. The systematic name may generally include the full name and all short forms, as those created and developed by the International Union of Pure and Applied Chemistry (IUPAC). The systematic name may also include names as defined or registered by third-party (other than the manufacturer) services, including, for example, Chemical Abstraction Service (CAS), Anatomical Therapeutic Chemical (ATC) Classification System, PubChem, DrugBank, ChemSpider, Unique Ingredient Identifier (UNII), Kyoto Encyclopedia of Genes and Genomes (KEGG), Chemical Entities of Biologic Interest (ChEBI), Chemical Database of the European Molecular Biology Laboratory (ChEMBL), etc. In addition to chemical or biological entities, the taxonomy may also include terms for medical devices, such as pacemakers; physical therapy device, such as massage chairs; consumer products, such as shavers, hair driers, etc. Such devices may have nicknames adopted by the user community over the years, in addition to a label as approved by regulatory agencies, such as the FDA, the EMA, MHRA, etc. These nicknames may be incorporated into the taxonomy of the database as well. To the extent that the use of a healthcare product is increasingly global, users may discuss a product in the users' native language. In such discussions, references to the healthcare product could also be made in the manufacturer's language. For example, Asian users may refer to the use of Viagra in the users' Asian native language or in English. In particular, such references may be made in an abbreviated form either in the users' native language or in English. To accommodate such scenarios, the taxonomy may include the terms as defined in multiple languages including the on-line users' native language and the manufacturer's native language. As a result, the taxonomy may incorporate the term definitions in a plethora of language libraries, including all short forms, abbreviations, acronyms, etc. For each language library, multiple character encoding implementations may be incorporated into the taxonomy of the database 118.

Database 118 may additionally include a set of linguistic rules. The set of linguistic rules may include logic operations for conducting text searches as well as quantitative indices for numerical weights for each hit. The logic operations may include Boolean search operators for text strings, such as, for example, disjunctive (OR), conjunctive (AND), and exclusive (NOT), etc. The logic operations may also include any combinations of the simple logic operations nested by, for example, quotation marks (including single quotes and double quotes), parenthesis, brackets, etc. The logic operations may further include textual string operations, such as concatenation, transposition, substitution, appending operations, etc. The logic operations may further include embedding wildcard criteria anywhere in a textual string. The logic operations may additionally include nexus criteria of search terms, for example, whether the terms sought after may be found next to each other, in the same sentence, within a number of letters, characters, words, or sentences, within the same paragraph, within the same posting/comment, within a number of postings, etc.

The log of on-line postings 112 may be analyzed based on the taxonomy (202). The analysis may be performed automatically by a computing system at part of the text mining engine 120. The computing system may include a distributed network of computers configured to search the log 112 according to load balancing tactics. The load balancing tactics may factor in the computing power of each computer system on the distributed network, the proximity of each computer system to the data being searched, the likelihood of hits when searching a particular portion of log 118. As the world is increasingly and globally interconnected, log 112 may include aggregated comments posted by users from anywhere the world, the contents of which may be stored similarly anywhere in the world. Thus, the computing load may be distributed accordingly to improve efficiency, latency, and throughput. The analysis may employ any programming or scripting language capable of supporting text string search, including, but limited to, Practical Extracting and Reporting Language (PERL), python, Ruby, PHP Hypertext Preprocessor (PHP), SmallTalk, Java, C, C++, etc.

At a particular on-line forum, the number of discussion threads may be hundreds of thousands per day. The number of comments in a given discussion thread may arrive in tens of thousands per minute. These above numbers may still be growing. Although a preliminary collection of postings may be identified based on keyword search or pattern matching, to zero in on the worthy posts for further analysis, quantitative metrics may be used to filter out the uninteresting information.

Text mining engine 120 may score the analyzed postings based on the taxonomy and the set of linguistic rules. Specifically, words defined in the taxonomy may be assigned corresponding weights. If a defined word has been identified in a particular posting, the weight corresponding to the defined word may be directed to a numerical score of the posting. The scoring may be cumulative. For example, if a defined word has occurred in a posting multiple times, the numerical score of the posting may include the corresponding weight of the matching term multiplied by the number of occurrence. In some implementations, however, the score accumulation may not be linear. In one configuration, the weight may be tapering off for later occurrences. In another configuration, the weight may be increasing for later occurrences. In yet another configuration, the weight may be initially increasing and then tapering off after a number of occurrences. The transition number may be adjustable, depending on the context.

The linguistic rules may be targeted at a particular adverse effect, such as, for example, skin rash. The linguistic rules may be targeted at a group of related adverse effects, such as, for example, skin rash, skin irritation, skin coloration, etc. The linguistic rules may be tailored to look for adverse effect(s) for one healthcare product or a group of healthcare products. The linguistic rules may also be developed for one manufacturer of healthcare product or a group of healthcare products.

Generally, the linguistic rules may include the assigned weight for each matching pattern. For example, if the matching terms occur within the same sentence, the assigned weight may be higher than if the matching terms occur with less proximity (for example, within the same paragraph, etc.). In some configurations, a proximity-dependent weighting may assign more weight to a posting if the matching terms are separated by fewer words. For example, the posting may receive more weight if the matching terms occur within five words than if the matching terms occur within ten words. In contrast, some configurations may favor postings with words more separated. In still other configurations, the proximity factor may not be monotonic. For example, the weight assigned to the posting may be maxed out for a certain range of word separations. Outside the range, either smaller or larger, the weight assigned to the posting may be reduced. The optimal range may be adjusted depending on the context of the discussion.

Moreover, the linguistic rule may include an additional weight to indicate how likely the postings may be relevant to the sought-after adverse effect(s), the healthcare product or the manufacturer being tracked. In some implementations, the linguistic rules may factor in the relevancy of the forum where the postings come from. For example, if the postings are directed at an on-line discussion forum for the healthcare product and sponsored by the manufacturer, the postings and each discussion thread may receive the most weight. Similarly, if the postings quote postings directed at the on-line discussion forum for the healthcare product, then the quoted link may cause additional relevancy weight to be allocated to the postings. In some configurations, if the postings cite established references, such as published articles or surveys regarding the healthcare product, the postings may also receive the additional relevancy score. Published articles or surveys may not be limited to scientific or academic journals, for example, Science, Circulation, Stroke, etc. Instead, published articles or surveys may include any media for popular medicine, such as WebMD, CNN-Health, etc.

In addition, the linguistic rules may take into account of the subject matter of the on-line discussion. The subject matter may indicate the context of the on-line discussion. For example, if the on-line discussion is about a group outing event, then the assigned weight may generally be low, as the context may be unlikely to facilitate an on-line discussion of the adverse effect of a healthcare product. On the other hand, if the on-line discussion is about treatment of a diseased condition, such as, for example, Alzheimer's, cancer, depression, erectile dysfunction, etc., then the context may be more likely to elicit a discussion about the healthcare product, and hence any adverse effects of the healthcare product.

Further, the linguistic rules may include another weight assignment to indicate the specificity of the description presented in the discussion. For example, if the posting merely mentions that "I have Crohn's disease," then, the posting may receive a numerical score of one point. If, however, the posting includes something like "I have Crohn's disease and I have rash," then the posting may receive three to five points in some configurations. If, the posting includes something along the lines of "I have Crohn's disease. I took mesalamine and I have rash," the posting may receive as much as seven points in some configurations. If, the posting is as specific as ""I have Crohn's disease. I took mesalamine yesterday and now I have rash on my back," the posing may receive as much as the full credit of ten points for specificity. Generally, the specificity factor may depend on the richness of the details provided in the discussion.

Numerical weighting may quantify each identified posting so that the identified postings can be ranked. Generally, on-lines users of an on-line resource may number in tens of millions. In some implementations, the weights of each identified postings may be aggregated for each discussion thread in which the postings belong. The aggregated weight for a discussion thread may provide a quantitative measurement for the particular discussion thread.

The numerical weight may yield a score and the score may be compared against a threshold (206). The threshold may function as a cut-off level to weed out postings of less interest in the identification of reports on potential adverse effects. In some implementations, the threshold comparison may be a multi-dimensional comparison so that the importance of each identified posting may be gauged in more than one dimension. Candidate dimensions may include, for example, the space proximity of keywords identified in each posting or a particular discussion thread, the context of the discussion thread, the specificity of references to a particular adverse effect in the identified posting, the degree of the relevancy to the healthcare product, etc. A multi-dimensional comparison may factor in multiple considerations as a refinement over comparing with one cut-off level. However, a multi-dimensional comparison may be more computation intensive and hence may incur more latency. Some implementations, however, may include a mechanism to hop between a single-factor comparison and a multi-factor comparison, depending on, for example, a computing load on a particular server allocated to the search. Other implementations may allow the comparison to be refined from a single-factor to multiple factors when, for example, the relevancy degree falls below a border line but remains above a baseline threshold for being relevant. Hence, the comparison, as well as the computation, may be adapted for a particular scenario in the semantics analysis.

Historically, medicine and biology are regarded as soft science for lack of formal logic when compared to other disciplines such as physical sciences disciplines. In a sense, problems in medicine and biology may be more likely addressed by empirical evidence rather than formal logic. Instead, fuzzy logic approaches find plentiful applications in the fields on medicine and biology. In one example, when determining whether an on-line comment or discussion thread is noteworthy for including mentions of potential adverse effects, fuzzy logic approaches may be employed in analyzing the textual contents. In the context of searching for potential adverse effects for a healthcare product, fuzzy logic may find a special niche in semantics analysis. As computing machines may be inherently better suited to perform strictly formal logic and arithmetic operations, a machine implementation for semantics analysis may attempt to mimic a fuzzy logic approach by building on a combination of formal logic and arithmetic blocks. The combination may be adapted for particular scenarios encountered in the semantics analysis.

If the score does not reach the threshold, then the corresponding posting or the entire discussion thread may be regarded as not containing useful information on adverse effects. Such postings or discussion threaded may be determined as uninteresting or less likely to include useful information on potential adverse effects of a particular healthcare product (208). The uninteresting postings or discussion threads may be filtered out from further analysis.

If the score reaches the threshold, the corresponding posting or the entire discussion thread may be flagged as likely including mentions of potential adverse effects (210). The flagged postings or discussion thresholds may be elevated or bubbled up from the large volume of postings as leads that are worthy of attention by entities who may not be part of the discussion thread. The elevation of flagged postings may involve sending an email alert, a short message service (SMS) alert, or any form of texting that involves Internet Relay Chat (IRC). In elevating the flagged postings as priority listings prioritizing, duplicate postings, for example, in the same discussion thread, or in discussion threads at different on-line discussion forums, may be consolidated. In other words, duplicate comments may be identified and removed.

The elevated postings or discussion threads may serve as leads to potential adverse effects resulting from consuming a particular healthcare product. The elevated potential leads may be presented as hyperlinks in a report. A digest may be automatically generated based on the keywords identified in the postings. The elevated potential leads may be further analyzed (212). As discussed above, computer implementations may be inherently based on strict logic and arithmetic operations. Yet, semantics analysis in the context of medicine and biology may be better suited for fuzzy logic. Hence, leads identified by a computer implementation may be reviewed by, for example, a human expert. The human expert can be a drug safety expert with sufficient training in toxicology. The human expert may review the elevated leads to determine whether the potential adverse effects are indeed mentioned in postings or discussion threads. In some configurations, however, a computer server may perform detailed analysis to triage the elevated potential leads and narrow down a short list of potential leads for review by the human reviewer. The potential leads that are not on the short list may nonetheless be accessible, if the human reviewer decides to search for other leads related to those leads on the short list.

If further analysis reveals that the elevated leads do include credible and verifiable mentioning of adverse side effects that may be caused by consuming the healthcare product, the human expert may also compile a report to be submitted to the manufacturer. The safety department of the manufacturer, may further analyze the report and may subsequently notify regulatory agencies (214), such as, Federal Drug Administration (FDA), EMA (European Medicines Agency) of the European Union, MHRA (Medicines and Healthcare Products Regulatory Agency (MHRA) of United Kingdom. The manufacturer, however, may not be required to report, under agency rules, to the regulatory agencies with regard to the potential adverse effects as mentioned in the postings. The manufacturer may, however, choose to respond to the postings, for example, in the same discussion thread or separately in a press release. Such responses to unsolicited inquiries may improve an interactive dialog between consumers and the manufacturer. Generally, regulatory agencies highly encourage the interactive dialog between consumers and the manufacturer. A lack of response may be disadvantageous to the public image of the manufacturer. A timely and courteous response, on the other hand, can ease consumer concerns and enhance the public perception of the manufacturer.

Results of further analysis may be collected as feedback to fine-tune the database (216). Subsequently, refined database may be generated for analysis and scoring of future postings on the same or similar healthcare product with comparable adverse effects.

Figure 3A:
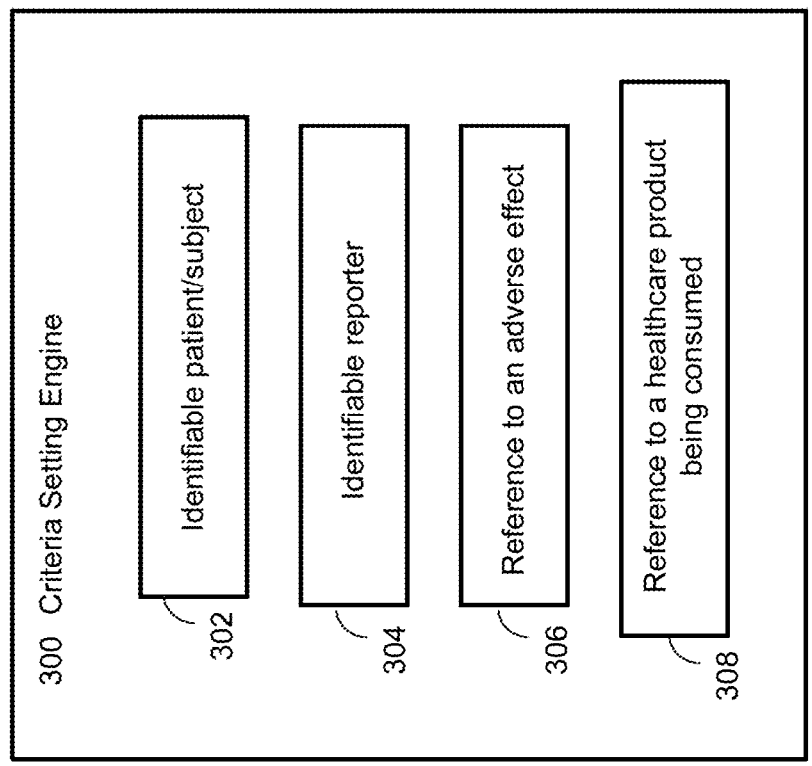
FIG. 3A shows a criteria setting engine for ascertaining potential AE reports resulting from consumption of a healthcare product according to some implementations.

FIG. 3A shows a criteria setting engine for ascertaining reports of potential adverse effects resulting from consuming a healthcare product according to some implementations. The criteria include features that may be mandatory to qualify a posting for analysis of adverse effects. Example criteria setting may include: setting an identifiable patient/subject; setting an identifiable reporter; setting a reference to an adverse effect; setting a reference to a healthcare product. Generally, such criteria may present binary factors. For example, identifiable patient/subject may ensure a person can be identified as suffering from an adverse effect. The person may be reached for verification if, for example, the discussion thread is at an on-line venue requiring registration. Likewise, an identifiable reporter may ensure a person witnessing the adverse effect may be identified. The witness person may be the patient him/herself. The witness person may also be a relative or friend of the patient. For the witness person to be an identifiable reporter, the witness person may need to have witnessed the adverse effect on his/her own. In other words, an identifiable reporter may not be a person who had merely heard about the adverse effect from someone else, who may be the identifiable reporter. Similarly, the postings may need to have references to both the healthcare product and adverse effect before the postings can be analyzed.

Figure 3B:
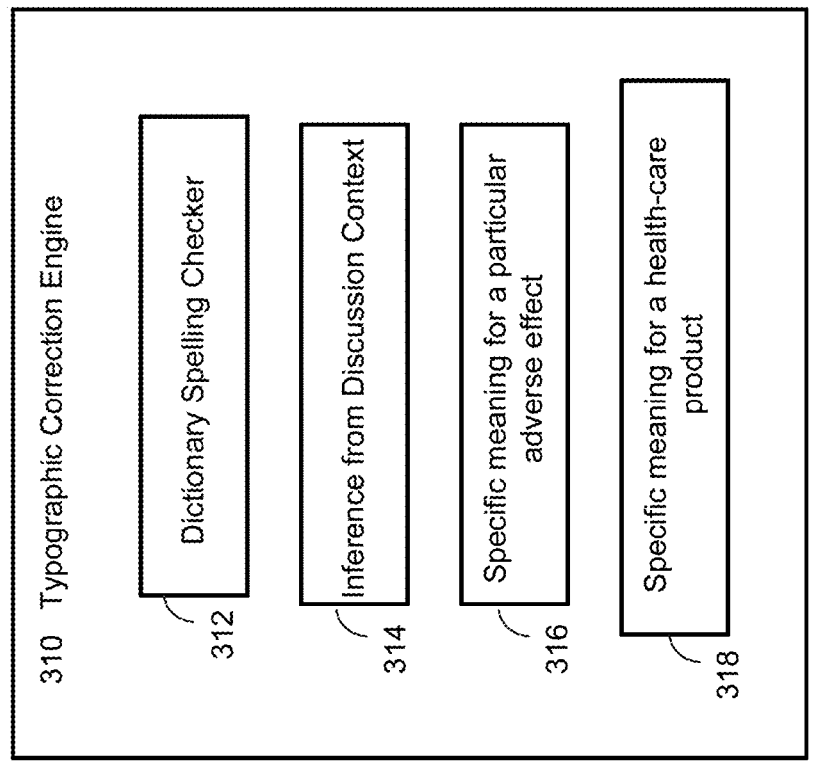
FIG. 3B shows a typographic correction engine for identifying potential AE reports resulting from consuming a healthcare product according to some implementations.

FIG. 3B shows a typographic correction engine 310 for identifying reports of potential adverse effects from consuming a healthcare product according to some implementations. Typographic engine 310 may include dictionary spelling checker 312, an engine for making inference from discussion context 314, an engine for determining specific meaning for an adverse effect 316, and an engine for determining specific meaning for a healthcare product 318. Dictionary spelling checker 312 may include a standard dictionary. Because the postings may be made by immigrants whose native language may not be English or by citizens of other countries who may not speak English, the standard dictionary may generally be multi-lingual. The engine for making inference 314 may be configured to correct typos in view of the discussion context. For example, a user may wish to enter "I have rash." However, due to limited space on a touch screen, the user actually entered "I have trash," even though the user meant he/she had rash. If other postings in the same discussion thread are regarding skin conditions including rashes, then inference checker 314 may correct the word "trash" to "rash." On the other hand, if some postings in the same discussion thread mention diarrhea, or other digestive issues, then inference checker 314 may not make corrections to the word "trash." Engine for determining specific meaning for a particular adverse effect 316 may correct spellings when a special word exists for describing the particular adverse effect. For example, when the discussion is about mental side effects of taking a drug, engine 316 may more likely cause a correction of "happe" as "happy," rather than "happen." Similarly, engine for determining specific meaning for a particular healthcare product may influence the correction of a particular word in view of the particular healthcare product being discussed. For example, when the healthcare product being discussed is an ecstasy pill, engine 318 may more likely cause a correction of "feeling hight" as "feeling high," rather than "feeling right."

Figure 3C:
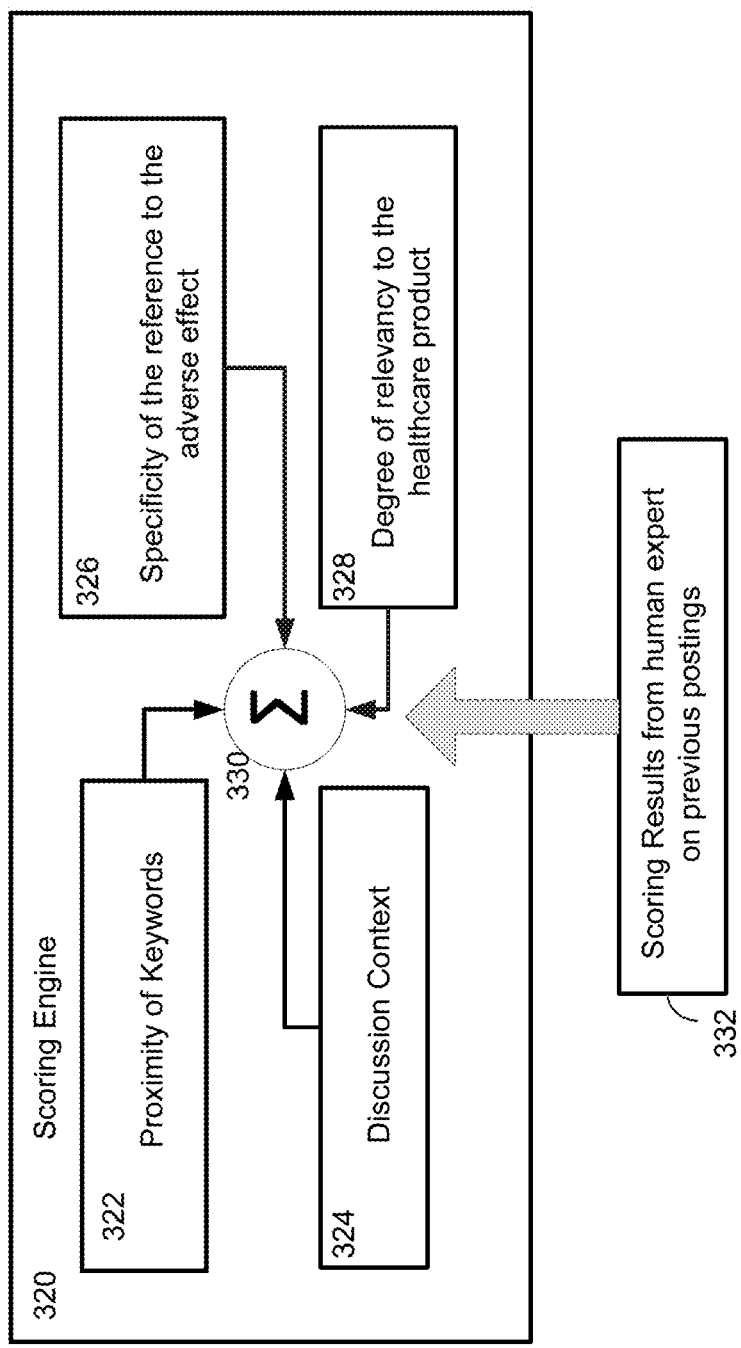
FIG. 3C shows a scoring engine for ranking potential AE reports resulting from consuming a healthcare product according to some implementations.

FIG. 3C shows a scoring engine for identifying reports of potential adverse effects from consuming a healthcare product according to some implementations. In some implementations, each posting and each discussion thread may be scored based on proximity of keywords 322, discussion context 324, specificity of reference to the adverse effect 326, and degree of relevancy to the healthcare product 328. Proximity factor 322 may refer to the special separation of the identified keywords in a particular posting or discussion thread. Depending on how far apart the identified keywords are spaced, the corresponding posting and discussion thread may receive a commensurate weight, as discussed above. Discussion context 324 may generally refer to the subject matter of a discussion as well as the circumstantial information associated with the keywords as identified in the postings or the discussion thread. Discussion context may render it more or less likely for a posting or discussion thread to mention a potential adverse effect from consuming a healthcare product, as discussed above. Specificity factor 326 may generally reflect the level of details being revealed specifically about the adverse effect. Relevancy factor 328, on the other hand, may generally indicate the how on point the contents of the discussion are, with regard to potential adverse effects resulting from consuming the healthcare product. For each factor discussed herein, a numerical weight may be assigned to indicate quantitatively the corresponding score for the factor. The assignment scheme, i.e., the weight for a particular factor under a certain scenario, may be adaptively adjusted based on feedback of previous results.

In some implementations, the scoring results may be reviewed by a human expert who may revise the scoring results based on additional consideration. The additional considerations may be necessitated when viewing the entire discussion as a whole. A machine implemented automatic process may be more consistent with a reductionist approach in which tasks may be broken down into subtasks. Each subtask may be further divided into items which may be divided again. Such a reductionist approach may reflect a divide-and-conquer philosophy with the assumption that each task may be broken down, sometimes iteratively, to a lowest level at which the problem becomes manageable and solutions of the puzzle at the lowest level will propagate upward, leading to a solution of the entire puzzle. However, the isolationist approach may not adequately reflect the interrelationship between the subparts. In other words, a summation of solutions of each subpart may be less than an optimal solution for the problem as a whole. Yet, an integrationist approach may require human intelligence to address the problem as a whole. Nonetheless, such intelligence may be emulated by a process known as machine learning. In particular, a machine implemented scheme may adaptively adjust the criteria or conditions involved in decision-making, based on examples from past experience. Such past experience may, at least in part, come from results of human endeavor or feedback. As an illustration, a human expert may inspect the automatically generated score, revise and confirm the vocabulary, verify typographic error identified and corrected, and validate linguistic rules to rate the postings. Results of manual inspection, revision, confirmation, verification, and validation may be used as feedback in a knowledge-based system to augment and adjust rules employed by the knowledge-based system.

In the case of the scoring engine 320, automatic scoring results may be reviewed and revised by a human expert. The human expert may be well versed on the safety aspects of a particular healthcare product. For example, an expert of the adverse effects of a drug may be thoroughly familiar with drug safety or toxicology issues associated with the drug. An expert of the adverse effects of a medical device may be a device safety expert. The human expert may render judgment regarding the overall quality of a bubbled-up posting or discussion thread. In rendering the judgment, the human expert may rate the bubbled-up posting or discussion thread. As illustrated in FIG. 3C, scoring results 332 are from the human expert who has rated postings previously identified automatically by the scoring engine 320.

In one configuration, scoring results 332 may be used as feedback to scoring engine 320 so that scoring engine 320 may adjust the weights assigned to each factor under the corresponding circumstances as previously identified such that the scoring results based on the new weight assignments would yield scoring results more similar to scoring results 332 under these corresponding circumstances. For example, contributions from various factors may be combined as a weighted sum. In such an arrangement, feedback from scoring results 332 can cause one factor to be weighed more preferentially while another factor to be weighed less favorably, in a particular scenario as identified in the corresponding circumstances. Moreover, such weight assignment may be performed iteratively as more data is received and analyzed based on the revised database or as current data is being re-analyzed based on the revised database.

In another configuration, scoring engine 320 may be used to adjust how various factors are being computed so that new scoring result by scoring engine 320 under these corresponding circumstances would be more comparable to scoring results 332 from the human expert. As an illustration, initially, a particular factor, say, the proximity factor may be computed such that the importance tapers off as the separation of identified keywords increases. After receiving feedback, the proximity factor may be computed to highlight sweet spot in the separation of identified keywords, in which case, the importance tapers off when the separation increases or decreases from the sweet spot. Similar to the weight assignment adjustment, the computation adjustment may also be conducted iteratively as more data is received and analyzed based on the revised database or as current data is being re-analyzed based on the revised database.

In yet another configuration scoring engine 320 may be used to adjust the manner in which the contributions from various factors are combined so that new scoring result by scoring engine 320 under these corresponding circumstances would be more comparable to scoring results 332 from the human expert. For example, initially, a simple combination may simply add up the contributions from the factors. After receiving feedback, the combination scheme may be adjusted towards a non-linear combination in which some factors may be combined into the summation at an accelerated pace than other factors. The combination scheme may also be adjusted to inject a level of cross-correlation between the various factors such that the factors being combined are no longer independent of each other.

In some configurations, the adaptive learning process may also engage a genetic algorithm so that evolutionarily refined weight and computation schemes may yield results more and more similar to scoring results 332 from the human expert under the same circumstances. Moreover, some configurations may engage neutral networks designed to incorporate additional weighted factors to accommodate the complexity of the scoring process. The neural networks may also inject interconnections between various weighted factors so that an altered weigh for one factor can trigger altered weights for other factors.

Notably, scoring results 332 may serve as feedback to adjust the inner workings of typographic correction engine 310, illustrated in FIG. 3B, including, for example, engine 314 for making inference from discussion context, engine 316 for determining special meaning in the context of an adverse effect, and engine 318 for determining special meaning in the context of a healthcare product. As discussed above, the adjustment to the typographic correction engine 310 may be conducted iteratively. Both genetic algorithm and neural network designs may be incorporated by the adaptive learning process.

Scoring results may results 332 may additionally serve as feedback to refine healthcare taxonomy in database 118. Based on the feedback from scoring results 332, for example, new terms may be added to the healthcare taxonomy to accommodate the peculiarities of a new healthcare product. Likewise, terms that are unused or obsolete may be removed from the healthcare taxonomy. In a similar vein, terms may be modified to reflect, for example, special meanings for the new healthcare product being tracked in on-line postings, etc.

The superiority of the revised database may be demonstrated by improved sensitivity or specificity in detecting useful leads to adverse effects. Because the revised database may include refined terms, improved manner to combine scores from various contributing factors, or weights better tuned to a particular adverse effect, all things being equal, the revised database is expected to outperform the standard database (such as MeSH) for the automatic detection of meaningful mentions of adverse effects. In order words, the incidences of false positives and false negatives from the automatic detection engine should be reduced. Such improvements in automatic detection may translate into faster turn-around time for automatic detection, reduced manual review time, shortened report time of an adverse effect, reduced cost to manufacturers in developing a healthcare product, and ultimately lowered healthcare cost to our society.

The following excerpts show pseudo codes for an adverse effect (AE) tracker according to some implementations.

The coding example starts with loading the data log.

```
Begin Data load Process
If (external data) then
    Analyze the data;
    Load the data into the system;
```

-continued

```
Elseif (web data) then
    Create feeds to pull the data from internet based on provided
    data set;
    Refresh the feeds periodically to get new data;
Endif.
End Data load Process
```

The coding example then proceeds with a content categorization process.

```
Begin Content Categorization Process
Insert unique id of the data into categorization process and mark the flag
it as "Not Processed";
Select the data whose flag status as Not Processed;
For each record from the record set Do
    Read the record;
    Get Content;
    Get Content ID;
    If ((Content Body Text is not null) && (LengthOf(Content Body
    Text) > 0)) Then
        CategorizeRecordForEachAEOntology('Content Body
        Text', 'Content ID')
    Else
        Mark the record as "Categorization Done"
    EndIf
Done
End Content Categorization Process
```

The coding example also includes subroutines for the categorization process, as shown below.

```
Function CategorizeRecordForEachAEOntology('Content Body Text', 'Content ID') Do
    Define array of terms found in ontology;
    Define array of terms found in all ontologies;
    Define rank as zero;
CategorizeRecordForSingleOntology('Content Body Text','Content ID','SideEffects
Ontology ID','reference to the array of terms found in ontology','reference to the array of terms
found in all ontologies');
    If (at least one term found from SideEffects) Then
        Rank = 5;
    EndIf
    CategorizeRecordForSingleOntology('Content Body Text','Content
ID','PotentialAdverseEvents Ontology ID','reference to the array of terms found in
ontology','reference to the array of terms found in all ontologies');
    If (at least one term found from PotentialAdverseEvents) Then
        Rank = Rank + 2;
    EndIf
    CategorizeRecordForSingleOntology('Content Body Text','Content ID','AdverseEvents
Ontology ID','reference to the array of terms found in ontology','reference to the array of terms
found in all ontologies');
    If (at least one term found from AdverseEvents) Then
        Rank = Rank + 1;
    EndIf
    CategorizeRecordForSingleOntology('Content Body Text','Content ID','MeshDiseases
Ontology ID','reference to the array of terms found in ontology','reference to the array of terms
found in all ontologies');
    If (at least one term found from MeshDiseases) Then
        Rank = Rank + 1;
    EndIf
Mark the record as "Categorization Done"
Update the record with the computed final Rank
Done
Function CategorizeRecordForSingleOntology('Content Body Text','Content ID','Relevant
Ontology ID','reference to the array of terms found in ontology','reference to the array of
terms found in all ontologies') Do
Set Variable 'Core Term Done For Content ID' = 0;
Query and select the set of term names and term IDs that belong to the 'Relevant Ontology ID';
For each record from the record set Do
Get Term Name;
Get Term ID;
Set Variable 'Term Done For Content ID' = 0;
```

```
If ('Term Name' RegExp match in the 'Content Body Text' ) Then
    If ('Core Term Done For Content ID' = 0) Then
        Tag the Content with the 'Core Term' from the 'Relevant Ontology';
        'Core Term Done For Content ID' = 1;
    EndIf
    If ('Term Done For Content ID' = 0) Then
        Tag the content with 'Term Name';
        'Term Done For Content ID' = 1;
    EndIf
EndIf
If ('Term Done For Content ID' = 1) Then
    Continue While Loop;
EndIf
Query and select the term synonyms that belong to the 'Relevant Ontology ID' and the current
'Term ID';
Get Term Synonym Name;
For each record from the record set Do
If ('Term Synonym Name' RegExp match in the 'Content Body Text' ) Then
    If ('Core Term Done For Content ID' = 0) Then
        Tag the Content with the 'Core Term' from the 'Relevant Ontology';
        'Core Term Done For Content ID' = 1;
    EndIf
    If ('Term Done For Content ID' = 0) Then
        Tag the content with 'Term Name';
        'Term Done For Content ID' = 1;
    EndIf
EndIf
Done
Done
Done
```

Figure 4A:
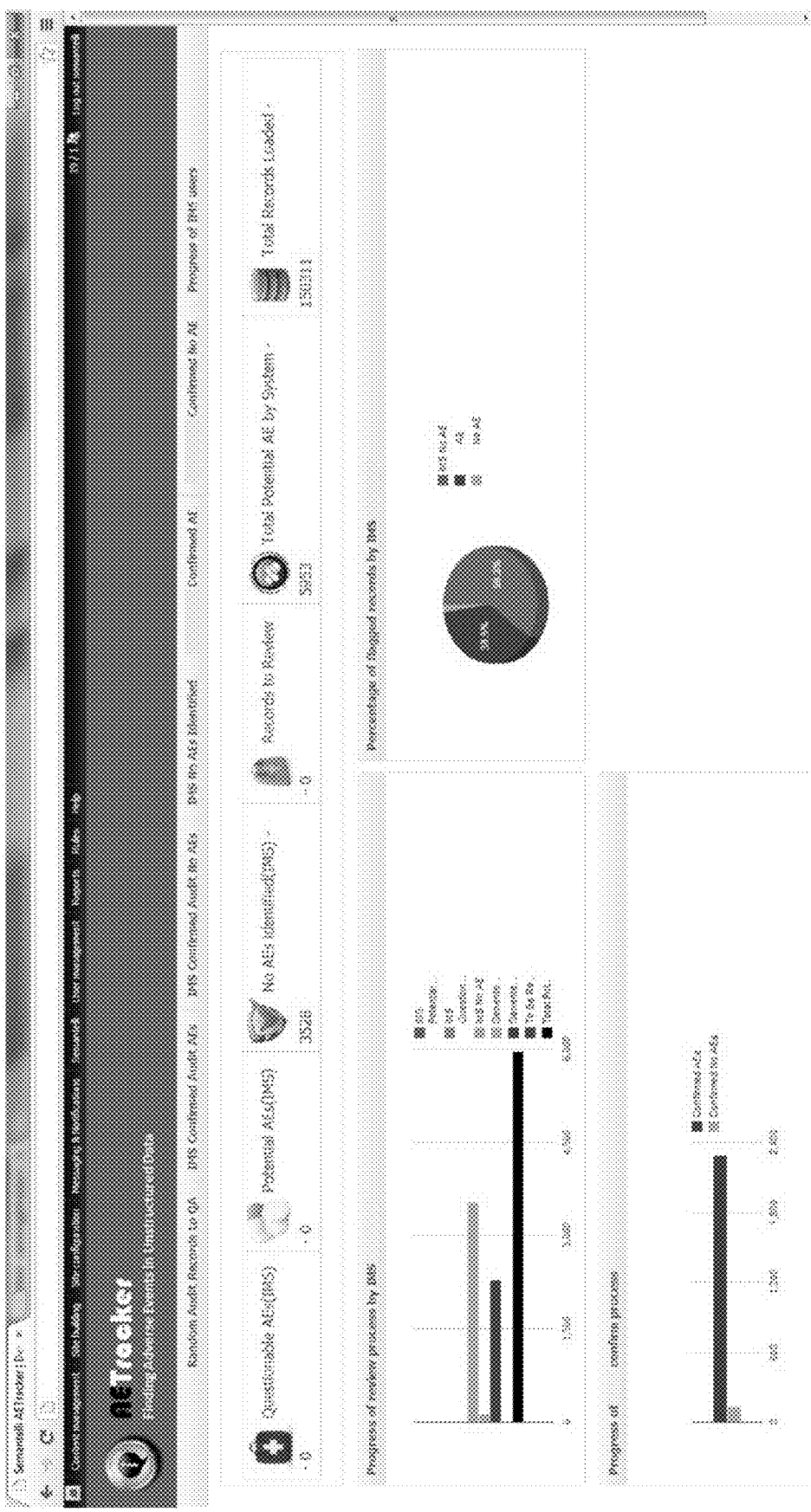
FIG. 4A shows an example user interface for presenting the summary result of tracking adverse effects according to some implementations.

FIG. 4A shows an example user interface for presenting the summary result of tracking adverse effects according to some implementations. After analyzing 150,311 records, the AE tracker system identified 5,953 leads to potential adverse effects. Either the manufacturer, or a third party entity, may review the identified leads to determine whether the comments are indeed worth noting and if further actions need to be taken. This user interface provides a convenient dashboard for a user to visualize results from the AE tracker system.

When the identified leads have been reviewed, some may be determined as worthy of further investigation, for example, contacting the author/report or the patient. Others, however, may be ignored for deficiency of meritorious information. A summary status chart may indicate the aggregate status of the identified leads.

Figure 4B:
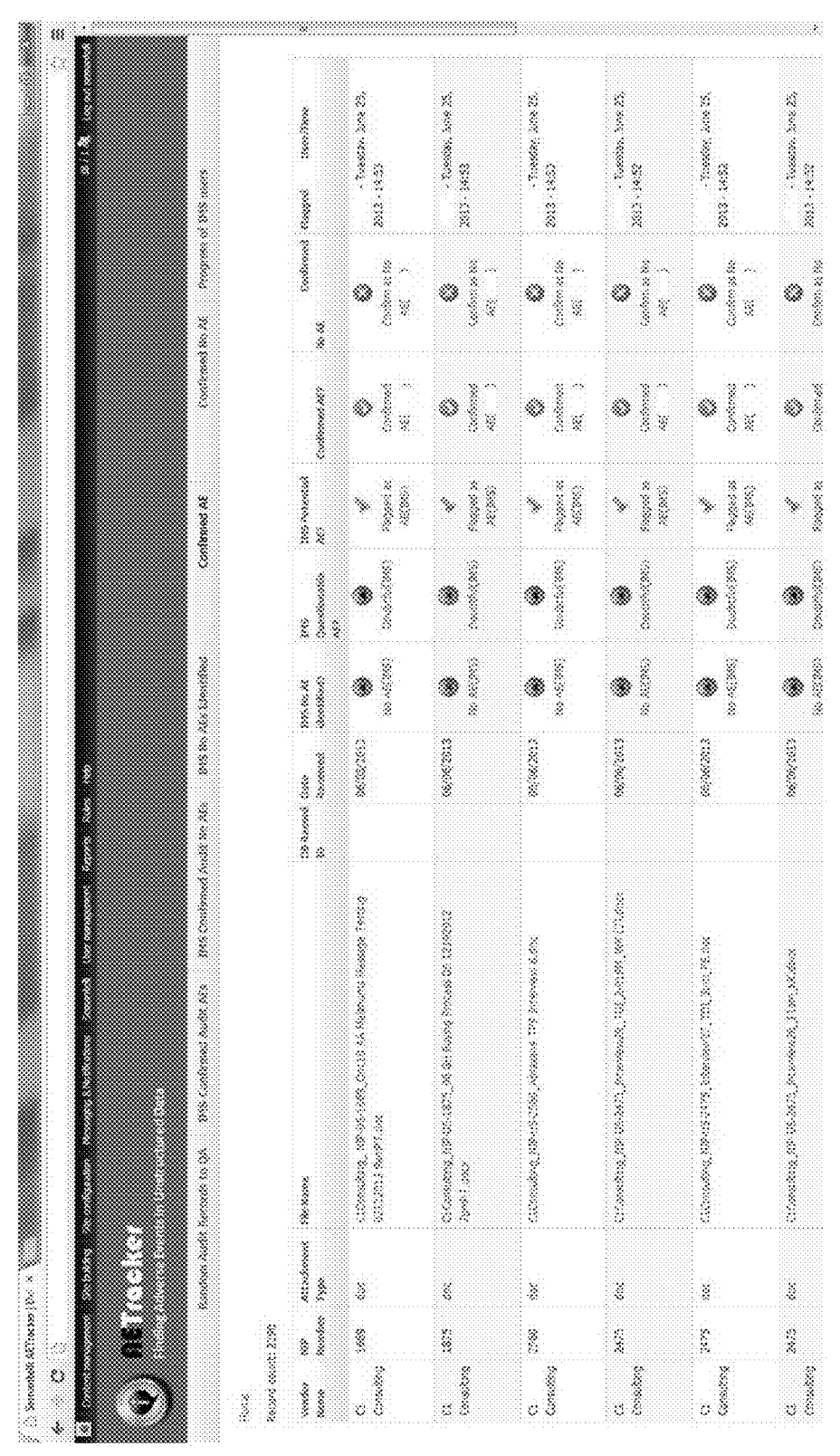

FIG. 4B shows another example user interface for reporting summary status of identified leads to adverse effects. Each row in FIG. 4B includes an entry showing whether the manufacturer has confirmed the identified lead as a potential adverse effect.

Figure 4C:
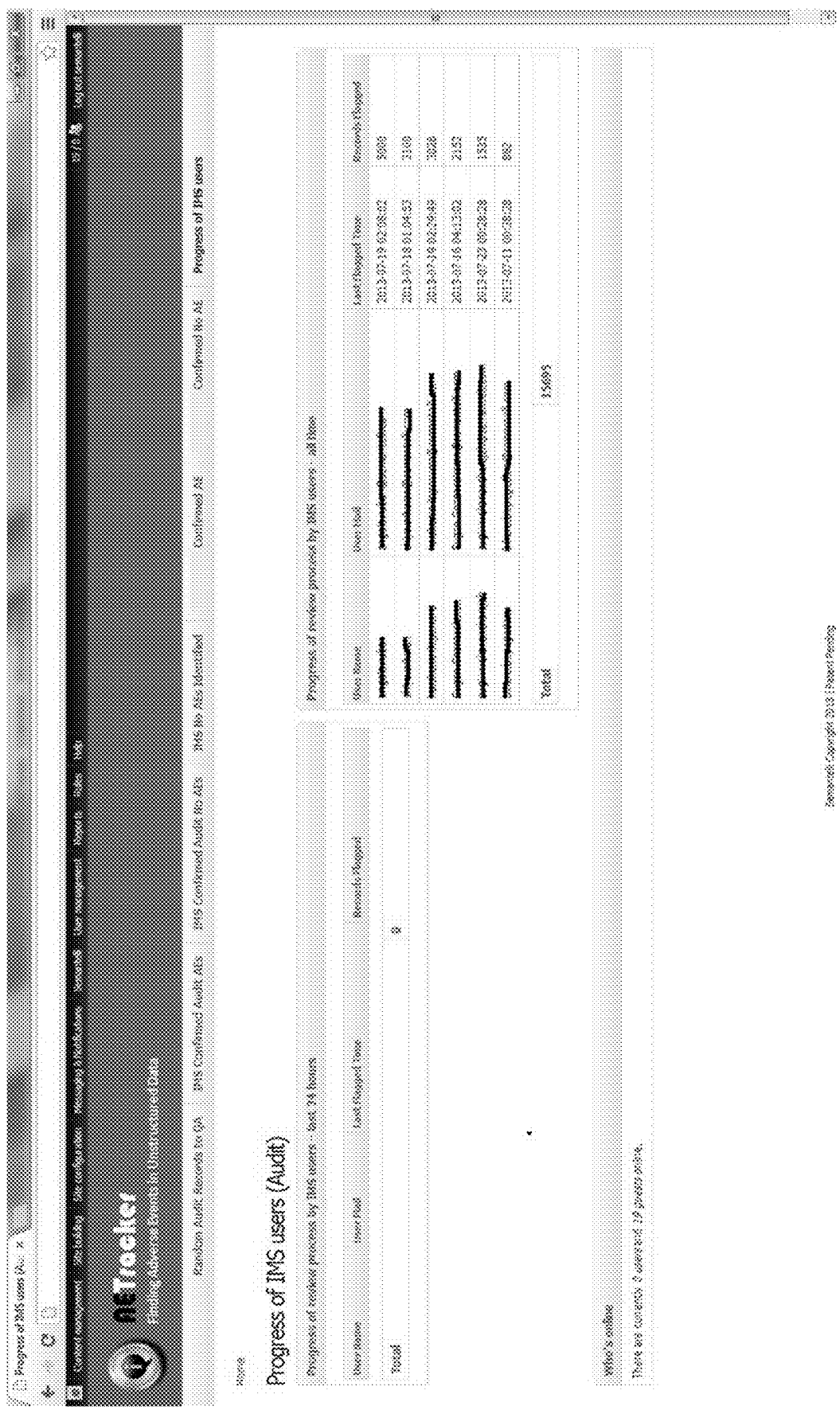
FIG. 4C shows yet another example user interface for reporting the progress of manual validation of the identified leads to adverse effects.

The progress of a reviewing party to inspect the identified leads may be reported. FIG. 4C shows yet another example user interface for reporting the progress of manual validation of the identified leads to adverse effects. The right panel of FIG. 4C includes a table showing the progress of review process by the reviewing party as a user of the AE tracker system.

Figure 4D:
FIGS. 4D to 4G are various snapshots of still another example user interface for configuring the vocabulary of a healthcare taxonomy for identifying side-effects.
Figure 4E:
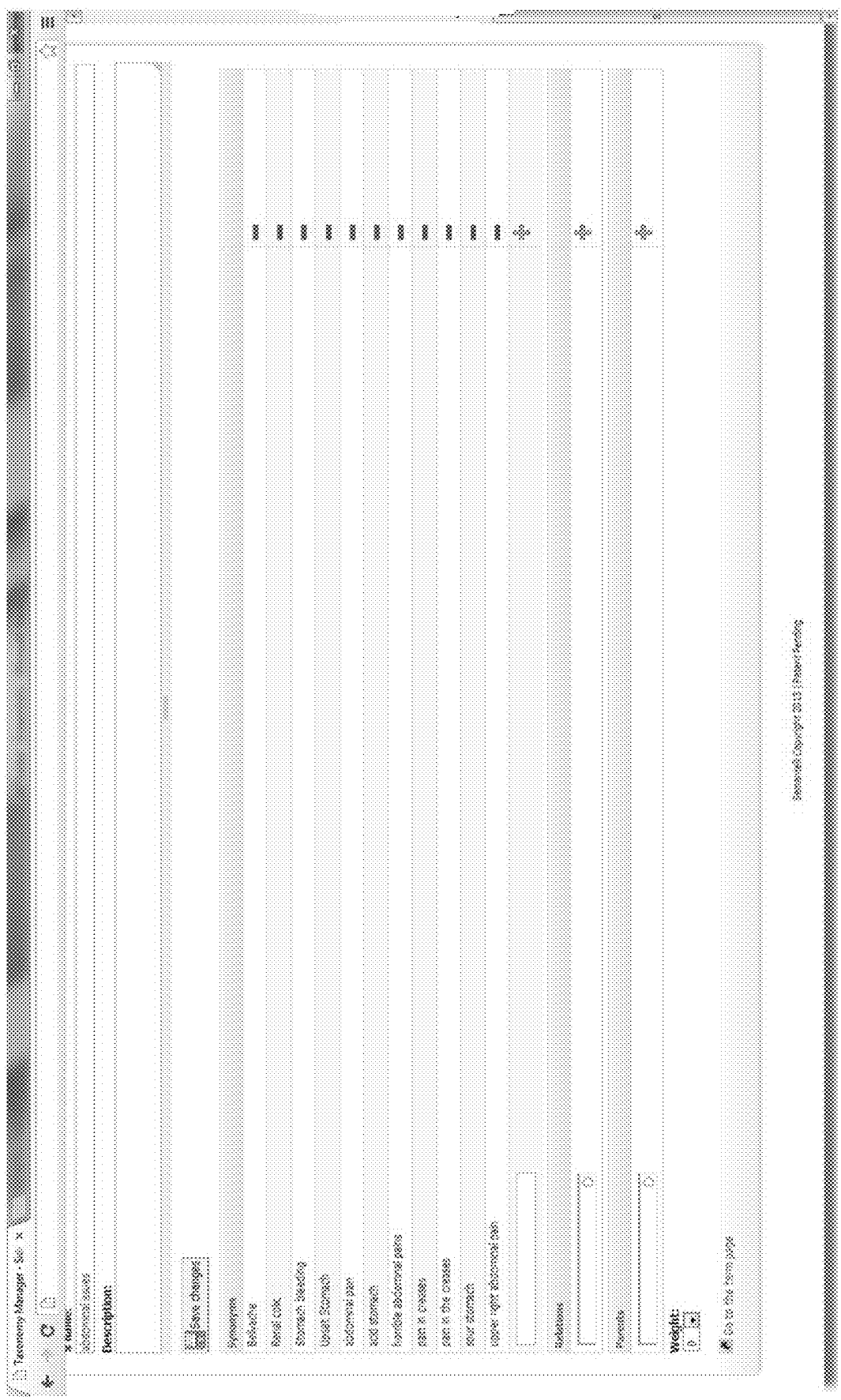
Figure 4F:
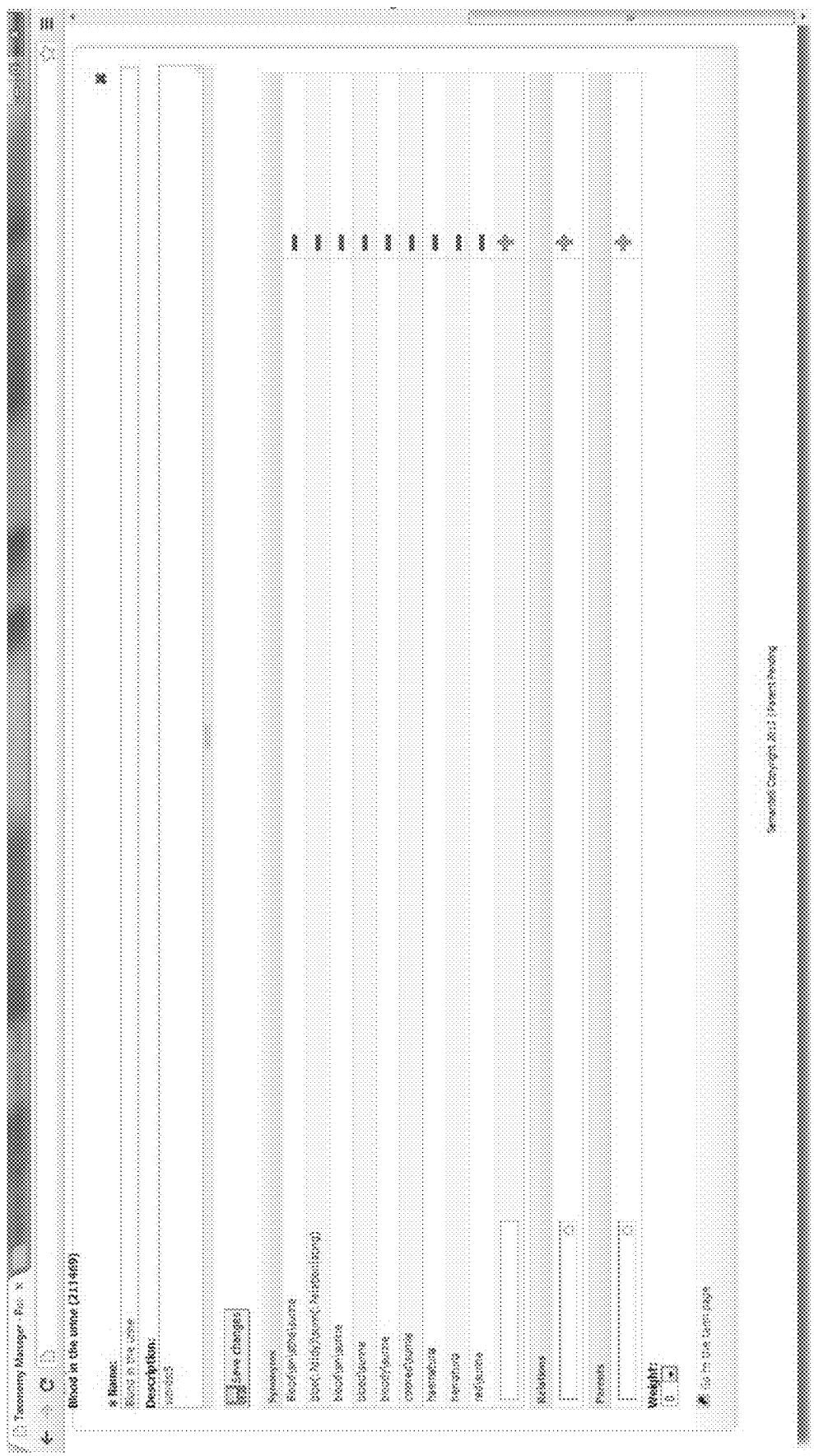
Figure 4G:
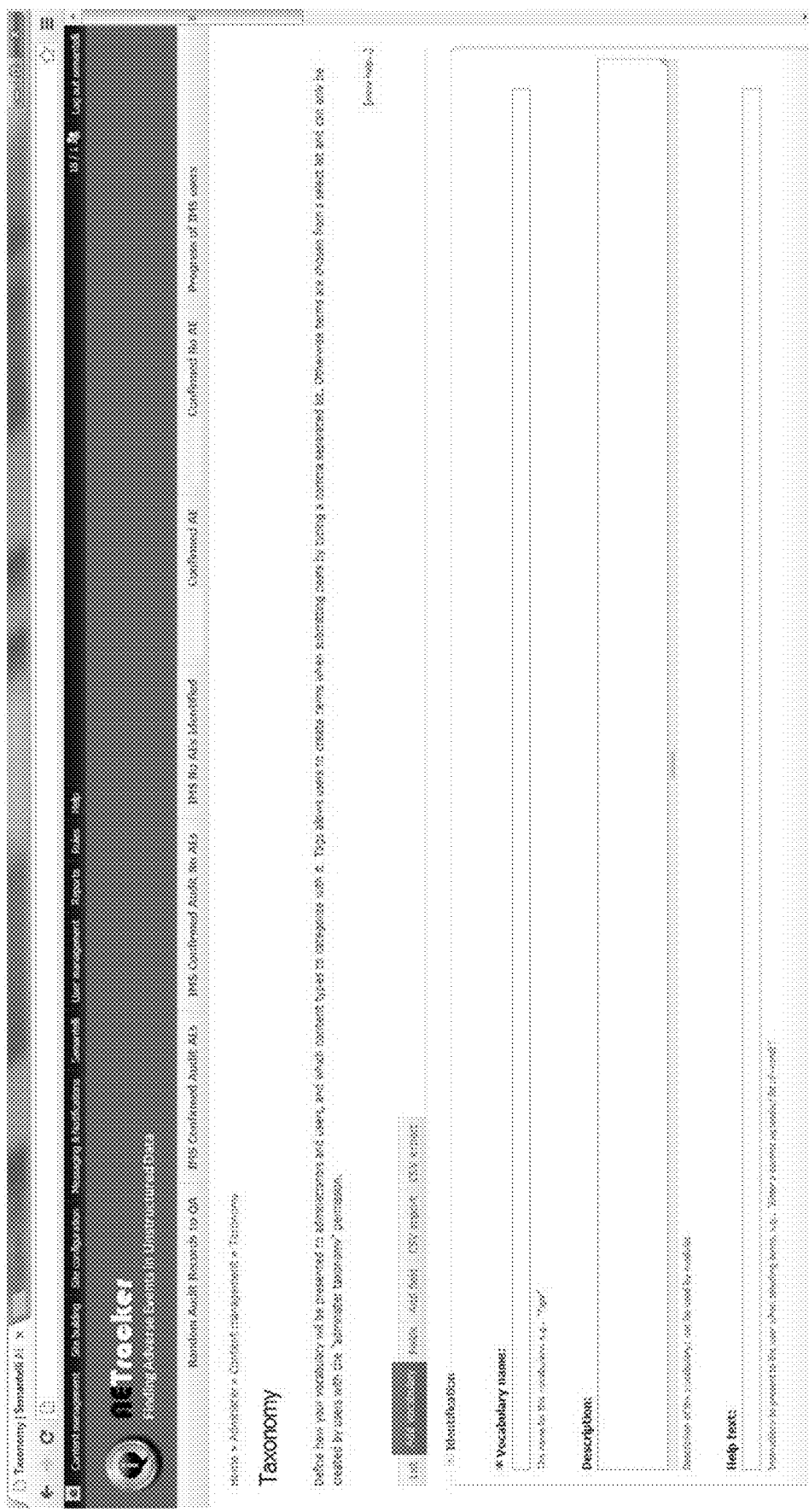

FIGS. 4D to 4G are various snapshots of still another example user interface for configuring the vocabulary of a healthcare taxonomy for identifying side-effects. FIG. 4D shows an interface for displaying existing terms in the taxonomy. FIG. 4E shows all synonyms of a particular term, "abdominal issues." FIG. 4F shows the linguistic patterns that may be interpreted to mean "blood in the urine." The vocabulary may be expanded and FIG. 4G shows an interface for a user of AE tracker system to enter new terms.

Figure 4H:
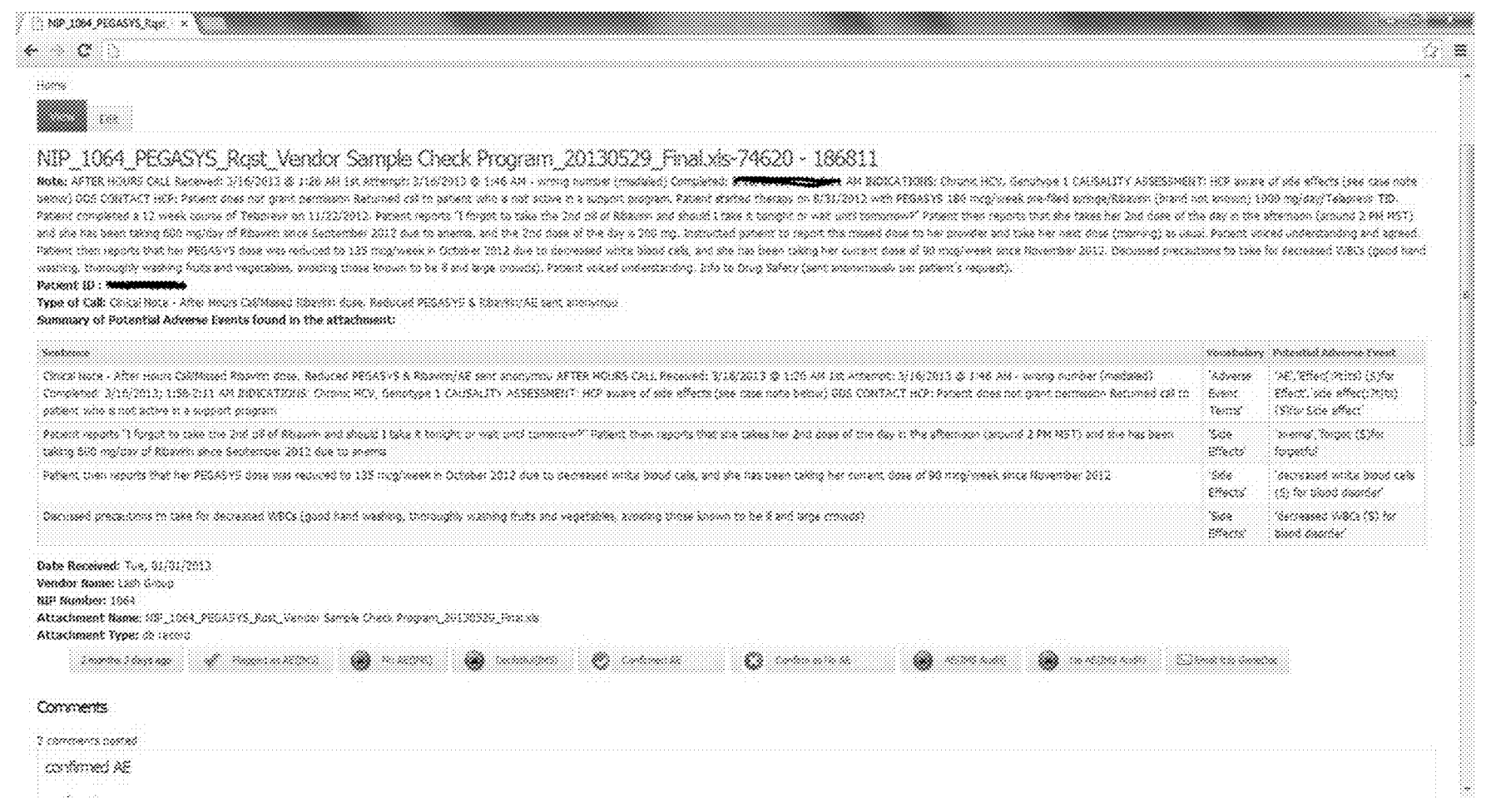

FIG. 4H show yet still another example user interface for presenting an identified lead to adverse effects once the lead has been confirmed. For example, based on the natural language processing techniques discussed herein, the AE tracker system may single out discussions or conversations with mentions of being forgetful (amnesia) or decreased white blood cells.

Implementations of the subject matter and the functional operations described in this specification can be implemented in digital electronic circuitry, in tangibly-implemented computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible non-transitory program carrier for execution by, or to control the operation of, data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including, by way of example, a programmable processor, a computer, or multiple processors or computers. The apparatus can also be or further include special purpose logic circuitry, e.g., a central processing unit (CPU), a FPGA (field programmable gate array), or an ASIC (application-specific integrated circuit). In some implementations, the data processing apparatus and/or special purpose logic circuitry may be hardware-based and/or software-based. The apparatus can optionally include code that creates an execution environment for computer programs, e.g., code that constitutes processor firmware, a protocol stack, a database management system, an operating system, or a combination of one or more of them. The present disclosure contemplates the use of data processing apparatuses with or without conventional operating systems, for example Linux, UNIX, Windows, Mac OS, Android, iOS or any other suitable conventional operating system.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., a central processing unit (CPU), a FPGA (field programmable gate array), or an ASIC (application-specific integrated circuit).

Computers suitable for the execution of a computer program include, by way of example, can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The memory may store various objects or data, including caches, classes, frameworks, applications, backup data, jobs, web pages, web page templates, database tables, repositories storing business and/or dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube), LCD (liquid crystal display), or plasma monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or GUI, may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN), a wide area network (WAN), e.g., the Internet, and a wireless local area network (WLAN).

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a sub-combination or variation of a sub-combinations.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be helpful. Moreover, the separation of various system modules and components in the implementations described above should not be understood as requiring such separation in all implementations, and it should be understood that the described program components and systems can generally be integrated together in a single software product or packaged into multiple software products.

Particular implementations of the subject matter have been described. Other implementations, alterations, and permutations of the described implementations are within the scope of the following claims as will be apparent to those skilled in the art. For example, the actions recited in the claims can be performed in a different order and still achieve desirable results.

Accordingly, the above description of example implementations does not define or constrain this disclosure. Other changes, substitutions, and alterations are also possible without departing from the spirit and scope of this disclosure.

The invention claimed is:

1. A computer-implemented method, comprising:
    assigning, by a computer processor, weights to words of a healthcare taxonomy;
    consolidating, by a reader interface, postings of multiple online forums into a log of postings;
    filtering, by a criterion setting engine, the log of postings based on a search parameter to identify a subset of the postings that relate to an adverse effect resulting from consuming a healthcare product;
    identifying, by the computer processor, a portion of the words of the healthcare taxonomy in the log of postings;
    generating, by a text mining engine, a relevance score for each of the postings of the subset of postings based on linguistic rules and the weights assigned to the words of the healthcare taxonomy identified in the respective postings;
    selecting, by the computer processor, postings for which the relevance scores meet a threshold;
    receiving, by the computer processor, feedback regarding precision of the relevance scores of the selected postings;
    adjusting, by the computer processor, the weights assigned to the words of the healthcare taxonomy identified in the selected postings in accordance with the feedback; and
    repeating the consolidating, the filtering and the generating based on the adjusted weights;
    wherein the consolidating comprises,
        sending requests to multiple search engines and/or databases by a metasearch engine of the reader interface, and
        aggregating results of the requests into the log of postings by a feed aggregator of the reader interface.

2. The method of claim 1, wherein the generating includes text mining the log of postings based on natural language processing using the linguistic rules.

3. The method of claim 2, wherein the filtering comprises searching the log of postings for an identifiable consumer of the healthcare product, an identifiable reporter of a posting, a reference to the adverse effect resulting from consuming the healthcare product, and/or a reference to the healthcare product.

4. The method of claim 2, further comprising identifying, with a typographic correction engine, typographic errors in the log of postings based on a discussion context.

5. The method of claim 4, further comprising correcting the typographic errors with the typographic correction engine according to the discussion context, a special meaning in a context of the adverse effect resulting from consuming the healthcare product, and/or a meaning in a context of the healthcare product.

6. The method of claim 1, wherein the assigning comprises assigning the weights based on contributions from a proximity of keywords, a discussion context, an amount of detail with regard to the adverse effect resulting from consuming the healthcare product, and a relevancy degree with regard to the healthcare product, as defined in the linguistic rules.

7. The method of claim 1, wherein the assigning comprises weighing previous manual inspections for adverse effects comparable to the adverse effect resulting from consuming the healthcare product or comparable healthcare product.

8. The method of claim 1, wherein the postings comprise on-line postings from two or more of a social networking web-site, an on-line discussion forum, an on-line app-store, and a blogging web-site.

9. The method of claim 1, further comprising alerting, by the computer processor, a user of the selected postings.

10. The method of claim 9, wherein the alerting comprises sending an email alert, a short message service message, and/or a voicemail.

11. The method of claim 9, further comprising, by the computer processor:
    detecting and consolidating duplicate postings in the log of postings.

12. A system, comprising:
    a computer processor configured to assign weights to words of a healthcare taxonomy;
    a reader interface configured to consolidate postings of multiple online forums into a log of postings;
    a criterion setting engine configured to filter the log of postings based on a search parameter to identify a subset of the postings that relate to an adverse effect resulting from consuming a healthcare product;
    the computer processor further configured to identify a portion of the words of the healthcare taxonomy in the log of postings;
    a text mining engine configured to generate a relevance score for each of the postings of the subset of postings based on linguistic rules and the weights assigned to words of the healthcare taxonomy identified in the respective postings;

wherein the computer processor is further configured to, select postings for which the generated relevance scores meet a predefined threshold, receive feedback regarding precision of the relevance scores of the selected postings, and adjust the weights assigned to the words of the healthcare taxonomy identified in the selected postings in accordance with the feedback; and wherein the system is further configured to identify subsequent online postings that relate to the adverse effect resulting from consuming the healthcare product based on the adjusted weights assigned to the words of the healthcare taxonomy; and wherein the reader interface comprises,
a metasearch engine configured to send requests to multiple search engines and/or databases, and
a feed aggregator to aggregate results of the requests into the log of postings.

13. The system of claim 12, wherein the text mining engine is further configured to text mine the log of postings based on natural language processing using the linguistic rules.

14. The system of claim 13, wherein the criterion setting engine is further configured to search the log of postings for an identifiable consumer of the healthcare product, an identifiable reporter of a posting, a reference to the adverse effect resulting from consuming the healthcare product, and/or a reference to the healthcare product.

15. The system of claim 13, further comprising a typographic correction engine configured to identify typographic errors in the log of postings based on a discussion context.

16. The system of claim 15, wherein the typographic correction engine is further configured to correct the typographic errors according to the discussion context, a special meaning in a context of the adverse effect resulting from consuming the healthcare product, and/or a meaning in a context of the healthcare product.

17. The system of claim 12, wherein the computer processor is further configured to assign the weights based on contributions from a proximity of keywords, a discussion context, an amount of detail with regard to the adverse effect resulting from consuming the healthcare product, and a relevancy degree with regard to the healthcare product, as defined in the linguistic rules.

18. The system of claim 12, wherein the computer processor is further configured to weigh previous manual inspections for adverse effects comparable to the adverse effect resulting from consuming the healthcare product or comparable healthcare product when assigning the weights to the words of the healthcare taxonomy.

19. The system of claim 12, wherein the postings comprise on-line postings from two or more of a social networking web-site, an on-line discussion forum, an on-line app-store, and a blogging web-site.

20. The system of claim 12, wherein the computer processor is further configured to alert a user of the selected postings.

21. The system of claim 20, wherein the computer processor is further configured to send an email alert, a short message service (SMS) message, or a voicemail to alert the user of the selected postings.

22. The system of claim 20, wherein the computer processor is further configured to:
detect and consolidate duplicate postings in the log of postings.

23. The method of claim 1, wherein the adjusting comprises:
performing an adaptive learning process by the computer processor.

24. The method of claim 23, wherein the adjusting further comprises:
using a genetic algorithm to refine the weights to reduce differences between the relevance scores generated by the text mining engine and scores received in the feedback.

25. The method of claim 1, wherein the consolidating comprises:
retrieving postings from multiple web feeds with respective feed readers of the reader interface; and
aggregating the multiple web feeds into the log of postings by the feed aggregator of the reader interface.

26. The method of claim 1, wherein the generating comprises:
generating the relevance scores by the text mining engine over a distributed network of computer systems according to load balancing tactics that factor in computing power of each computer system of the distributed network of computer systems, proximity of the computer systems to postings of the log, and/or a likelihood of hits when searching respective portions of the log of postings, efficiency, latency, and/or throughput.

27. The method of claim 1, wherein the generating comprises:
generating the relevance scores by the text mining engine over a distributed network of computer systems according to load balancing tactics that factor in efficiency, latency, and/or throughput.

28. The system of claim 12, wherein the computer processor is further configured to:
adjust the weights with an adaptive learning process.

29. The system of claim 28, wherein the computer processor is further configured to:
adjust the weights with a genetic algorithm to reduce differences between the relevance scores generated by the text mining engine and scores received in the feedback.

30. The system of claim 12, wherein the reader interface comprises:
multiple feed readers, each to retrieve postings from a respective one of multiple web feeds; and
the feed aggregator to aggregate the multiple web feeds into the log of postings.

31. The system of claim 12, wherein the text mining engine is further configured to generate the relevance scores over a distributed network of computer systems according to load balancing tactics that factor in computing power of each computer system of the distributed network of computer systems, proximity of the computer systems to postings of the log, and/or a likelihood of hits when searching respective portions of the log of postings, efficiency, latency, and/or throughput.

32. The system of claim 12, wherein the text mining engine is further configured to generate the relevance scores over a distributed network of computer systems according to load balancing tactics that factor in efficiency, latency, and/or throughput.

* * * * *